United States Patent
Radhakrishnan et al.

(10) Patent No.: US 10,631,758 B2
(45) Date of Patent: Apr. 28, 2020

(54) MEASURING LUNG FUNCTION AND LUNG DISEASE PROGRESSION AT A LOBAR/SEGMENTAL LEVEL

(71) Applicant: PulmonX Corporation, Redwood City, CA (US)

(72) Inventors: Srikanth Radhakrishnan, Cupertino, CA (US); Surag Mantri, Sunnyvale, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 0 days.

(21) Appl. No.: 14/801,848

(22) Filed: Jul. 17, 2015

(65) Prior Publication Data

US 2016/0015295 A1 Jan. 21, 2016

Related U.S. Application Data

(63) Continuation of application No. 12/964,515, filed on Dec. 9, 2010, now Pat. No. 9,107,606.

(60) Provisional application No. 61/293,578, filed on Jan. 8, 2010.

(51) Int. Cl.
| | | |
|---|---|---|
| *A61B 5/08* | (2006.01) | |
| *A61B 5/085* | (2006.01) | |
| *A61B 5/087* | (2006.01) | |
| *A61B 5/00* | (2006.01) | |
| *A61B 5/097* | (2006.01) | |

(52) U.S. Cl.
CPC .............. *A61B 5/085* (2013.01); *A61B 5/087* (2013.01); *A61B 5/097* (2013.01); *A61B 5/6853* (2013.01); *A61B 5/7278* (2013.01); *A61B 2562/0247* (2013.01)

(58) Field of Classification Search
CPC ........... A61B 5/085; A61B 5/00; A61B 5/097; A61B 5/087; A61B 5/6853; A61B 5/7278; A61B 2562/0247
See application file for complete search history.

(56) References Cited

U.S. PATENT DOCUMENTS

| | | | |
|---|---|---|---|
| 4,667,669 A | 5/1987 | Pasternack | |
| 5,161,525 A | 11/1992 | Kimm et al. | |
| 5,720,709 A | 2/1998 | Schnall | |
| 5,876,352 A * | 3/1999 | Weismann | A61B 5/085 600/529 |

(Continued)

OTHER PUBLICATIONS

Gottfried, et al. Interrupter technique for measurement of respiratory mechanics in anesthetized humans. J Appl Physiol (1985). Aug. 1985;59(2):647-52.

(Continued)

*Primary Examiner* — Navin Natnithithadha
*Assistant Examiner* — Eric Messersmith
(74) *Attorney, Agent, or Firm* — Wilson Sonsini Goodrich & Rosati

(57) ABSTRACT

A method for determining lung function in a patient is disclosed, in which a multi-lumen catheter with an expandable occluding element at its end is used to isolate a targeted lung compartment, and respiratory characteristics at the targeted lung compartment are measured over multiple respiratory cycles. The relation between various characteristics of the respiratory cycle is used to determine compliance of lung tissue within the targeted lung compartment.

4 Claims, 12 Drawing Sheets

(56) References Cited

U.S. PATENT DOCUMENTS

| | | | |
|---|---|---|---|
| 6,066,101 | A | 5/2000 | Johnson et al. |
| 6,634,363 | B1 | 10/2003 | Danek et al. |
| 6,692,494 | B1 | 2/2004 | Cooper et al. |
| 7,094,206 | B2 | 8/2006 | Hoffman |
| 7,282,032 | B2 | 10/2007 | Miller |
| 9,107,606 | B2 | 8/2015 | Radhakrishnan et al. |
| 2003/0168066 | A1 | 9/2003 | Sallvin |
| 2006/0254600 | A1 | 11/2006 | Danek et al. |
| 2007/0142742 | A1 | 6/2007 | Aljuri et al. |
| 2007/0240717 | A1* | 10/2007 | Kaczka ............ A61B 5/085 128/204.21 |
| 2008/0200797 | A1 | 8/2008 | Kotmel et al. |
| 2008/0234595 | A1* | 9/2008 | Ranieri ............ A61B 5/085 600/538 |
| 2011/0313307 | A1 | 12/2011 | Radhakrishnan et al. |

OTHER PUBLICATIONS

Notice of allowance dated Apr. 10, 2015 for U.S. Appl. No. 12/964,515.
Office action dated Mar. 14, 2013 for U.S. Appl. No. 12/964,515.
Office action dated Sep. 25, 2013 for U.S. Appl. No. 12/964,515.

* cited by examiner

MEASURING LUNG FUNCTION AND LUNG DISEASE PROGRESSION AT A LOBAR/SEGMENTAL LEVEL

CROSS-REFERENCE TO RELATED APPLICATION

This application is a continuation of U.S. patent application Ser. No. 12/964,515, filed Dec. 9, 2010, which claims the benefit of Provisional Application No. 61/293,578, filed on Jan. 8, 2010, the full disclosures of which are incorporated herein by reference.

BACKGROUND OF THE INVENTION

1. Field of the Invention

This invention relates generally to medical methods and systems and more specifically to methods for assessing the functionality of lung compartments.

2. Description of the Related Art

Lung diseases are a problem affecting hundreds of millions of people worldwide. Chronic obstructive pulmonary disease (COPD), for example, is a significant medical problem affecting about 16 million people in the U.S. (or about 6% of the U.S. population) and many millions of people around the world. Lung cancer, as another example, is among the most prevalent forms of cancer, and causes more than 150,000 deaths per year. In general, two types of diagnostic tests are performed on a patient to determine the extent and severity of lung disease: 1) imaging tests, and 2) functional tests. Imaging tests, such as chest x-rays, computed tomography (CT) scans, Magentic Resonance Imaging (MRI), perfusion scans, and bronchograms, provide a good indicator of the location, homogeneity and progression of the diseased tissue. However, these tests do not give a direct indication of how the disease is affecting the patient's overall lung function and respiration capabilities. This can be measured with functional testing, such as spirometry, plethysmography, oxygen saturation, and oxygen consumption stress testing, among others. Together, these diagnostic tests are used to determine the course of treatment for the patient.

Currently available diagnostic tests for COPD, however, are limited in the amount and type of information that may be generated. For example, diagnostic imaging may provide information to the physician regarding which lung regions "appear" more diseased, but in fact a region that appears more diseased may actually function better than one that appears less diseased. Similarly, functional testing is performed on the lungs as a whole. Thus, the information provided to the physician is generalized to the whole lung and does not provide information about functionality of individual lung compartments, which may be diseased. Thus, physicians may find it difficult to target interventional treatments to the compartments most in need and to avoid unnecessarily treating compartments that are least in need of treatment. Therefore, in general, using conventional imaging or functional testing involving the whole lung, the diseased compartments cannot be differentiated, prioritized for treatment, or assessed after treatment for their level of response to therapy. Consequently, there is a need for better indicators of localized disease progression as well as methods for measurement of these indicators.

One useful indicator of disease progression is the elasticity of the airways of the given lung compartment. In a lung affected by a COPD such as emphysema, there is permanent enlargement of the alveoli due to the destruction of the walls between alveoli. The destruction of the alveolar walls reduces the elasticity of the corresponding lung compartment during the respiratory cycle. Loss of elasticity leads to collapse of the bronchioles, obstructing airflow out of the alveoli. Air becomes "trapped" in the alveoli, which reduces the ability of the lung to contract during exhalation. The reduced expansion of the lung during the next breath reduces the amount of oxygenated air available for gaseous exchange. Further, the trapped air also can compress adjacent, less damaged lung tissue, preventing it from functioning to its fullest capacity. It would therefore be advantageous to identify those portions of the lung that are most severely affected by COPD and treat those areas by localized lung volume reduction methods.

Localized diagnostic methods for identifying and quantifying diseased lung portions have been disclosed in the following co-pending U.S. Patent applications assigned to the assignee of the present application: U.S. Pub. Nos. 2007/0142742 and 2008/0200797, the full disclosures of which are hereby incorporated by reference. The '742 application discloses ways of locally measuring collateral ventilation, while the '797 application discloses several concepts for localized lung diagnostics including collateral ventilation and lung compliance measurement, and devices and systems for such measurement.

The detection of loss of elasticity of lung tissues is a method that would be desirable for tracking the progression of COPD in affected patients. In a normally functioning lung or compartment, the elasticity of the tissues enables expulsion of inhaled air, while in an affected lung or lung portion the loss of elasticity manifests as an inability to expel air. This is apparent in the various characteristics of inspiratory or expiratory air flow. For example, the pressure exerted during exhalation is a measure of lung elasticity, and local (lobar) measurement of exhalation pressure can provide an indicator of disease progression. Although pressure measurement has been used in relation to several types of respiratory conditions, there is no known use of exhalation pressure for diagnostic purposes.

Pressure measurements outside the body have been disclosed in other conditions, for example, in relation to sleep apnea. Such measurement of pressure during respiration is disclosed in several references such as U.S. Pat. No. 4,667,669 to Pasternack, U.S. Pat. No. 5,161,525 to Kimm et al. and U.S. Pat. No. 5,720,709 to Schnall. However, the apparatus disclosed in these applications measure pressure variations detected at the mouth or external to the lung. The pressure variations are therefore indicative of the properties of the entire lung and do not provide data from the diseased portions alone. U.S. Pat. No. 6,066,101 to Johnson et al. and U.S. Pat. No. 7,094,206 to Hoffman disclose methods of measuring respiratory resistance of the lungs. The system includes a pneumotach, into which the patient breathes normally. In both the references, the measurement method uses pressure transducers to measure pressure variations during inhalation and exhalation. The references further include methods for analysis of the data to obtain data on lung function and alveolar function. However, as with devices intended for sleep apnea, these methods are external and do not provide diagnostic information pertaining to localized diseased lung portions. Rather, they provide an average value for the entire lung. This is disadvantageous, as certain compartments maybe more affected by disease than others, yet since the diagnosis is of the entire lung, only the entire lung may be treated.

Pressure measurements within the lung have also been used in the diagnosis of asthma and emphysema, as disclosed in U.S. Pat. No. 6,634,363 to Danek et al. and U.S. Pat. No. 6,692,494 to Cooper et al. and U.S. Patent Application number 2006/0254600 to Danek et al. The '363 patent and the related '600 application concern asthma treatment and disclose diagnosing lung sensitivity to asthmatic stimuli by stimulation of a portion of the lung, followed by pressure measurement to detect constriction and reversible constriction of the airways. However, it does not reveal information on the elasticity of lung tissue that would aid in diagnosis of COPD. Similarly, the '494 patent discloses measurement of change in pressure within an occluded lung compartment. This measurement is made, however, for quantifying collateral ventilation, and does not provide information on lung tissue elasticity.

Therefore, it would be advantageous to have methods and systems for more accurately diagnosing and/or pinpointing COPD in the lungs. Ideally, such methods and systems would provide information regarding elasticity of the lungs, and more specifically information regarding elasticity of various portions of the same lung. In doing so, such lung assessment methods and systems would help a physician more accurately and effectively assess lung function and disease and thus develop more effective treatment strategies.

BRIEF SUMMARY OF THE INVENTION

The present application is directed toward measurement of tissue elasticity of local lung portions through the use of local pressure measurement during exhalation. A method for determining lung function, particularly elasticity of lung airways in a patient is disclosed. The method comprises introducing a multi-lumen catheter into an airway leading to a targeted lung compartment. The catheter comprises a distal end, a proximal end and a lumen therebetween. The distal end comprises an expandable occluding element which is configured to sealingly engage the airway, the proximal end comprises an inflation port to expand the occluding element, and the lumen is in-line with at least one sensor for measuring a respiratory characteristic. The targeted lung compartment that is fed by the airway is isolated by expanding the occluding element. At least one respiratory characteristic is measured to determine elasticity of the airway.

In one embodiment, the method comprises measuring airflow to and from the targeted lung compartment over a number of inspiratory and expiratory cycles; and determining the tidal flow volume during respiration. The relationship between the tidal flow volume, the airway pressure and changes in airway pressure over a number of inspiratory and expiratory cycles may then be determined. The method may further comprise determining the relationship between pressure and volume to determine the elasticity of the airway.

In another embodiment, the method comprises determining the volume of the targeted lung compartment as a function of time. A low decrease in volume over time during expiration indicates a diseased lung compartment.

The method may comprise determining the flow rate for a given volume of air expired or inspired into the lung. An unhealthy lung compartment will exhibit a lower flow rate for a given volume.

In yet another embodiment, the method comprises determining the flow rate for a given pressure within the targeted lung compartment, and diagnosing that the lung compartment is unhealthy, if the lung compartment exhibits a lower flow rate for a given pressure compared to the general population or to other lung compartments.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE INVENTION

Although the detailed description contains many specifics, these should not be construed as limiting the scope of the invention but merely as illustrating different examples and aspects of the invention. As such, the scope of the invention may include other embodiments not discussed in detail herein. Various other modifications, changes and variations may be made in the arrangement, operation and details of the methods and systems of the present invention disclosed herein without departing from the spirit and scope of the invention as described.

In one embodiment, a method is described for determining the elasticity of lung tissue in diseased lung compartments affected by COPD. Such compartments could be an entire lobe, a segment, a subsegment and beyond. Diagnosis is achieved by isolating a lung compartment at a desired assessment site and measuring pressure variations in the isolated lung compartment during breathing. The method is minimally invasive in the sense that the required instruments are introduced orally, and the patient is allowed to breathe normally during the procedures.

Figure 1A:
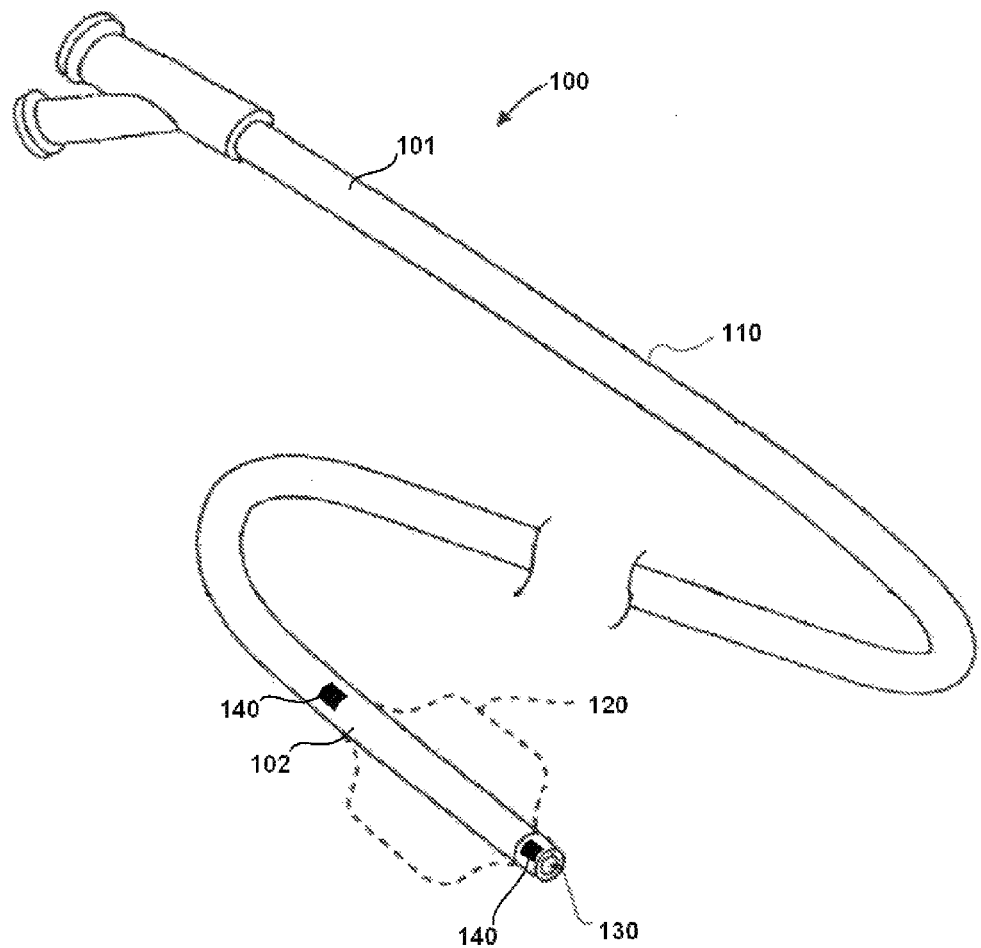
FIG. 1A shows a diagram of an isolation catheter in accordance with an embodiment of the present invention.
Figure 1B:
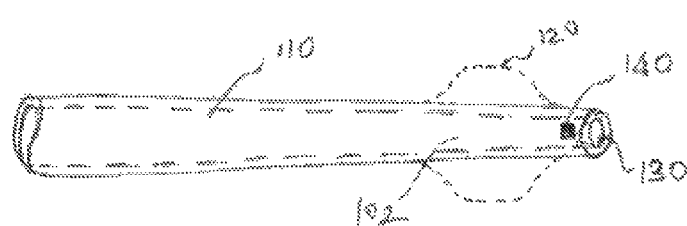
FIGS. 1B, 1C and 1D show alternative embodiments of the catheter for local measurement of a lung.
Figure 1C:
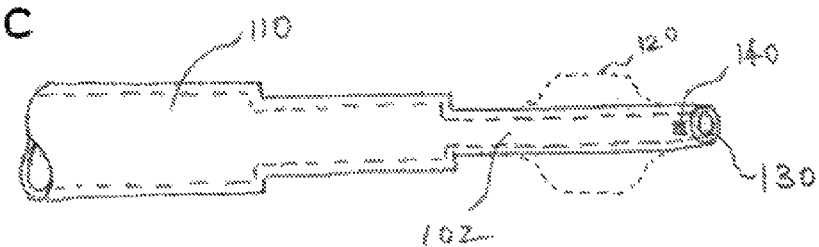
Figure 1D:
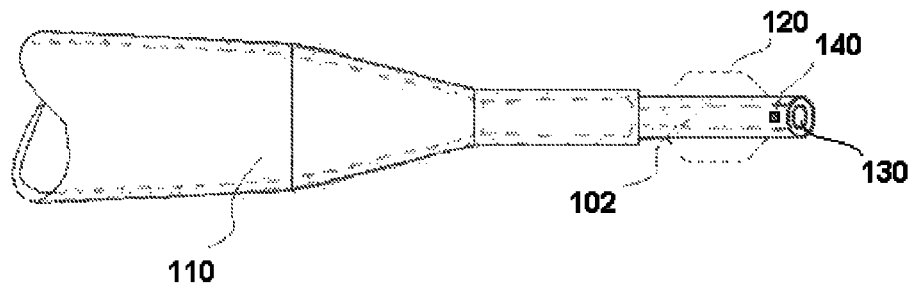
Figure 2:
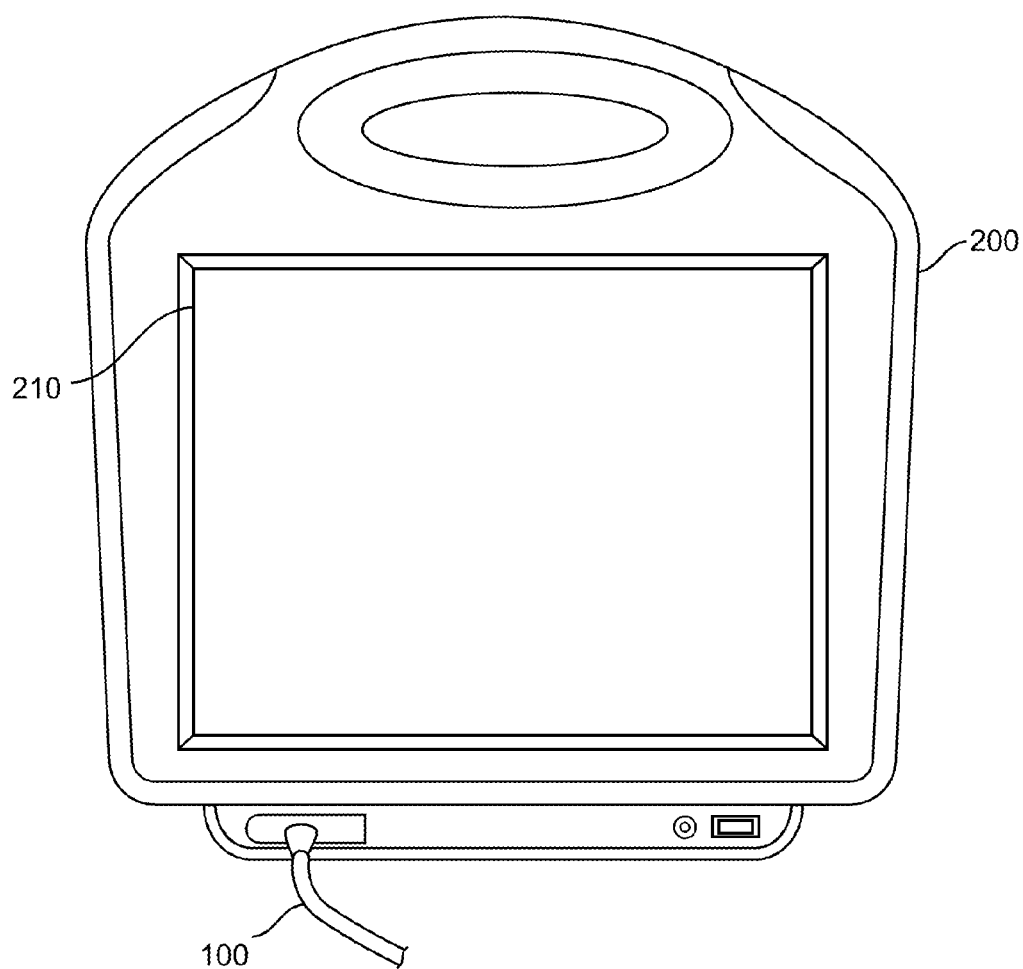
FIG. 2 shows a diagram of a control unit in accordance with an embodiment of the present invention.

In the present embodiments, isolation of the lung comprises sealingly engaging a distal end of a catheter in an airway feeding a lung compartment, as shown in FIGS. 1A and 2. Such a catheter has been disclosed in co-pending published U.S. patent application Ser. No. 10/241,733, which is incorporated herein by reference. As shown in FIG. 1A, the catheter 100 comprises a catheter body 110, and an expandable occluding member 120 on the catheter body. The catheter body 110 has a distal end 102, a proximal end 101, and at least one lumen 130, or alternatively multiple lumens, extending from a location at or near the distal end to a location at or near the proximal end. The proximal end of catheter 100 is configured to be coupled with an external control unit (not shown), and optionally comprises an inflation port (not shown). The distal end of catheter 100 is adapted to be advanced through a body passageway such as a lung airway. The expandable occluding member 120 is disposed near the distal end of the catheter body and is adapted to be expanded in the airway which feeds the targeted lung compartment. The catheter further comprises one or more sensors 140 that are located within or in-line with the lumen 130. The lumen of the catheter may be cylindrical and of a uniform diameter as shown in FIG. 1. In alternative embodiments shown in FIGS. 1B, 1C and 1D, the catheter lumen is configured to offer minimal resistance to airflow during exhalation and sampling. This is done so that the sampling process has a minimal effect on the flow or pressure characteristics being measured. Thus, in one embodiment of the catheter body 110 shown in FIG. 1B, the diameter may gradually taper from being broader at the proximal end to narrower at the distal end 102. In another embodiment shown in FIG. 1C, the diameter of the catheter body 110 may reduce in incremental stages from being broader at the proximal end to narrower at the distal end 102. In another embodiment shown in FIG. 1D, the catheter body 110 may have a combination of sections of varying degree of taper as well as of different uniform diameters. In the embodiment shown in FIG. 1D, for example, the distal-most section of the catheter is uniform in diameter and is configured to be held within a bronchoscope (not shown). Proximal to that distal portion is a portion that abruptly transitions to a larger diameter in order to engage with the valve of the bronchoscope. Thereafter, there is a slow transition to a third diameter as the catheter exits the bronchoscope.

The proximal end of the catheter 100 is configured to be associated with a control unit 200, as shown in FIG. 2. The control unit 200 comprises one or more measuring components for measuring one or more characteristics of respiration, for example, pressure, volume and flow rate. The measuring components may be integral with or disposed within the control unit 200. Optionally, control unit 200 may also comprise mechanisms to introduce a gas or a mixture of gases from a gas dilution unit into the isolated lung compartment via one or more catheter lumens. The control unit 200 comprises an interface for receiving input from a user and a display screen 210. The display-screen 210 will optionally be a touch-sensitive screen, and may display preset values. Optionally, the user will input information into the control unit 200 via a touch-sensitive screen mechanism. Additionally and optionally, the control unit may be associated with external display devices such as printers, or chart recorders. In some embodiments, the console 200 is configured to operate with continuously variable external resistances which can be applied through the catheter to the airway that it measures.

In the methods discussed below, at least a distal portion of the catheter body 110 is introduced and advanced into and through the trachea (T). The catheter may optionally be introduced through an introducing device such as a bronchoscope. The distal end 102 of the catheter 100 can then be directed to a lung compartment (LL) to reach an airway (AW) which feeds a targeted lung compartment (TLC), which is to be assessed. When the occluding element 120 is expanded in the airway, the corresponding compartment is isolated with access to and from the compartment provided exclusively through the lumen 130.

The occluding element 120 is then expanded to isolate the TLC with reference to the rest of the lung, and the patient is allowed to breathe normally over a number of respiratory cycles. Since airflow occurs through the lumen 130, the air exhaled from the TLC in particular will flow through the catheter 100 and into the control unit 200. Sensors 140 which are within or in-line with the lumen 130 are then used to measure the characteristics of air flow within the TLC. Optionally, a sensor 140 is located near the proximal end of the catheter 101 and would be used to measure the characteristics of the airflow at the mouth. Alternatively, the exhaled air at the mouth is measured from a sensor not associated with the catheter, and the data thus obtained is input manually or electrically (via wires) into the console. Additionally and optionally, the catheter comprises a closable valve (not shown), for example a solenoid valve, that is closable by a user.

Figure 4:
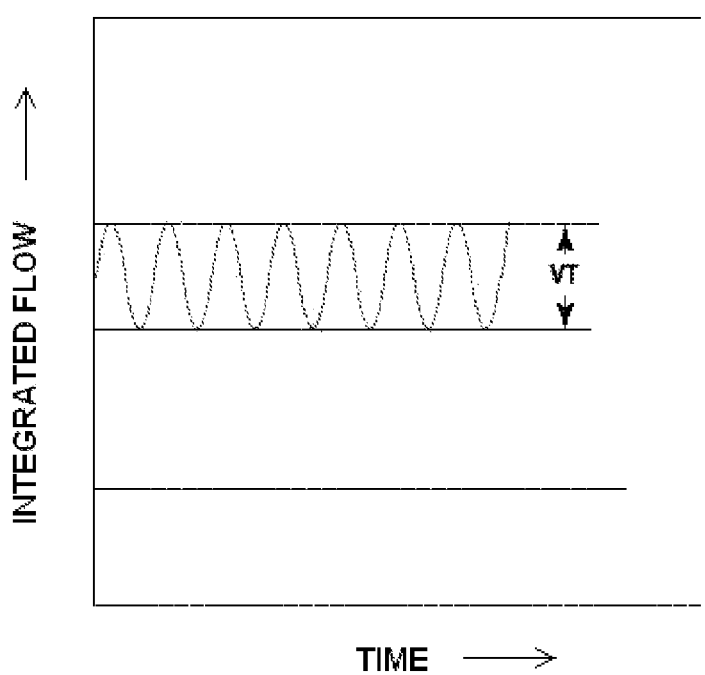
FIG. 4 shows a graphical representation of tidal flow during respiration.

With the catheter so placed, the compliance of the compartment, and corresponding diseased state of the compartment, can be determined using one of several methods. In one embodiment, the sensor 140 is configured to measure the flow of air through the airway at the site of occlusion passing to and from the targeted lung compartment TLC over a number of respiratory cycles. The tidal flow volume during respiration is determined as the average volume of air breathed in and out during normal breathing, as illustrated in FIG. 4, where VT is the measured tidal volume.

Simultaneously, the pressure within the airway can also be recorded for the corresponding tidal volumes. The static and/or dynamic compliance of the lung compartment can then be measured by analyzing the relationship between the tidal volume and changes in airway pressure during both inspiratory and expiratory cycles. Specifically, compliance may be measured by determining the pinpoint tidal volume for a given airway pressure at various points during respiration.

Figure 3:
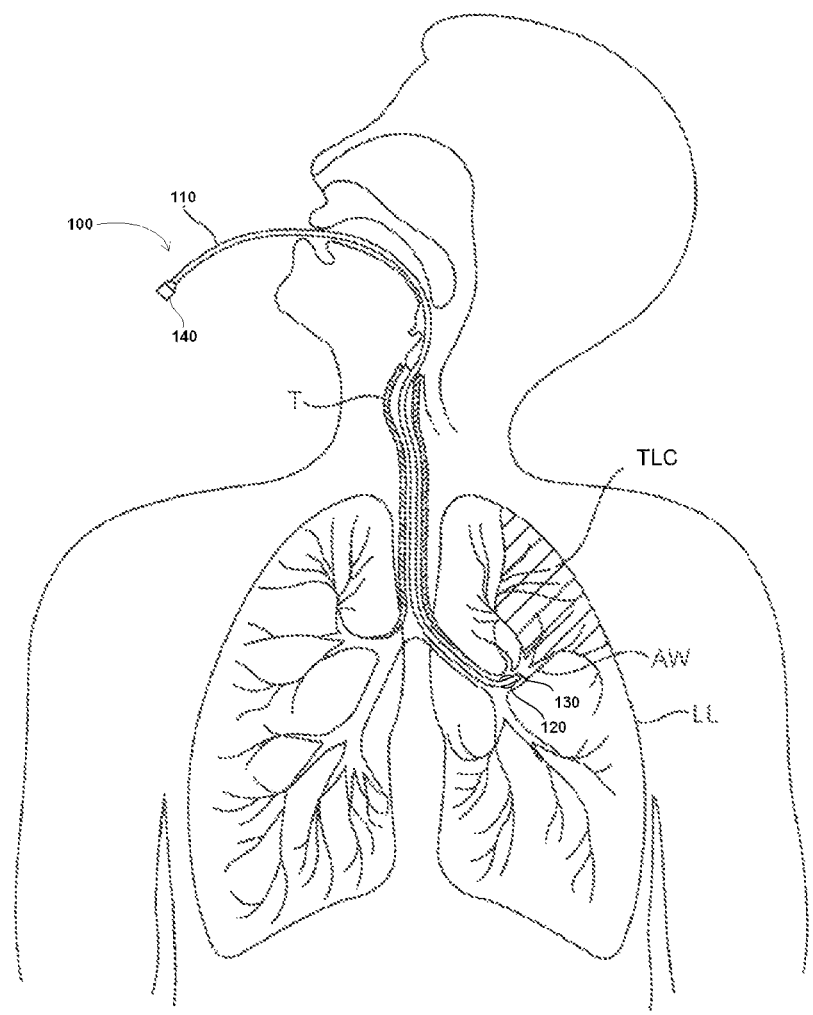
FIG. 3 shows the isolation catheter accessing a lung compartment.
Figure 5:
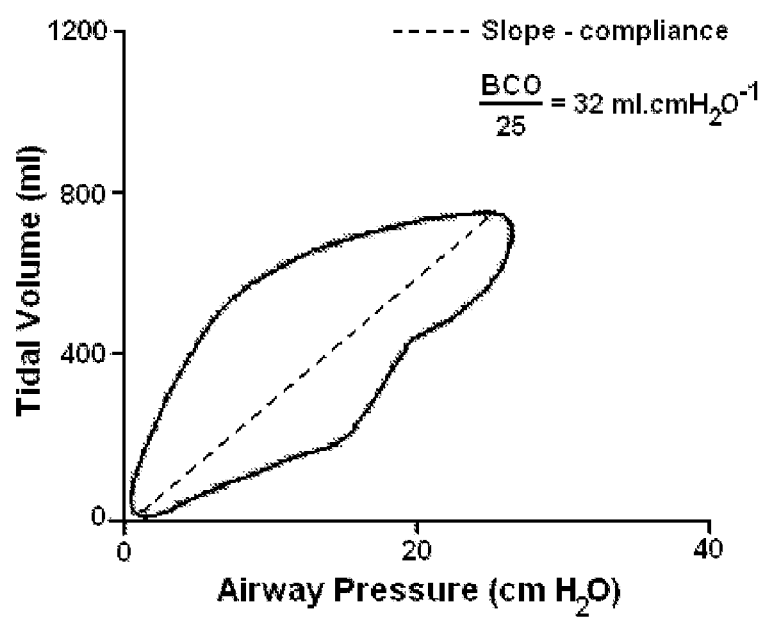
FIG. 5 shows the variation of tidal air volume versus airway pressure and determination of compliance.

For this method, the catheter 100 is used in conjunction with a solenoid valve, which is placed within or in-line with the lumen 130. With the catheter in place as shown in FIG. 3, both the tidal volume and the pressure generated by the TLC are measured during expiration. After normal values for the compartment are established, the solenoid valve is closed at a given point of respiration. Since the catheter is the only source of air flow to and from the TLC, the closing of the valve prevents airflow to the compartment. Pressure within the TLC is then measured when there is no airflow to the TLC. The process is repeated with the valve being closed at various points in the normal respiratory cycle. The resulting data points are plotted and exemplarily produce the graph that is shown in FIG. 5. The data points in the pressure-tidal volume curve are generated by conducting a pressure measurement at no flow (closed valve) states. When the procedure is repeated through the inspiratory and expiratory phases of a breathing cycle, a closed loop-like curve is obtained. The compliance of the lung compartment is then calculated as the slope of the curve .DELTA.v/.DELTA.p (the average slope) and is represented by the dashed line. Optionally, the process is repeated for the other compartments in the lung, and the values of different compartments within the same patient are compared. Alternatively, the values from a single compartment are compared to general population values. The lower the compliance is, the more diseased the compartment will be. Lung compartments with lower than normal values of compliance may then be selected for treatment.

Figure 6:
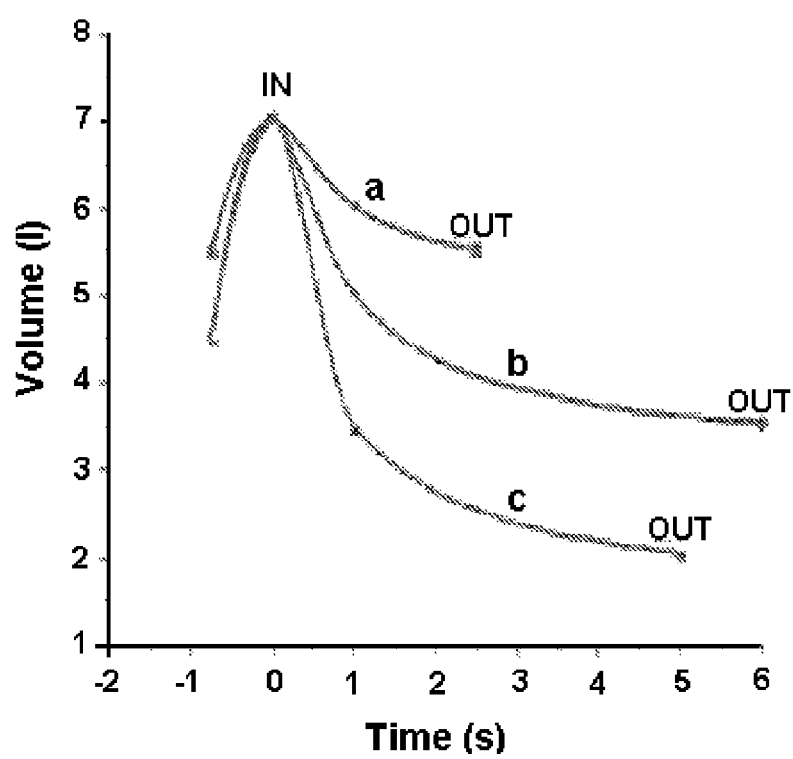
FIG. 6 shows the variation of flow volume with time from various lung compartments.

Alternatively, the volume of air during both inspiration and expiration can be measured over time. Diseased compartments will take a longer time for their volumes to be emptied, and any airflow obstruction will also reduce the speed at which the compartment can be emptied. Exemplary results of such measurements are shown in the graph in FIG. 6. In this graph, flow volume is shown as a function of time for both normal lung compartments and diseased lung compartments. Three exemplary curves are shown in this graph, each with a same peak volume ("In") that is obtained at the end of inspiration. Thereafter, during exhalation, fully diseased compartments (that are often hyperinflated) will exhibit the characteristics of curve "a" and will not empty by the end of exhalation ("Out"). Normal compartments that are able to force air out will exhibit the characteristics of curve "c", where low lung volumes are obtained quickly. Lungs that are progressing towards a diseased state will exhibit the in-between state with respect to both the change in volume and the remaining residual volume. In this instance, the compartment still empties and obtains a lower volume, but is does so at a slower rate than the healthy or normal compartment. Further, though the compartment empties more than a completely diseased one, it does retain a higher volume of air within the compartment than a healthy lung would. This is exemplarily characterized by curve "b". By comparing the compartments to each other or to the general population values and by looking for this in-between state, disease progression can both be detected and monitored.

Figure 7:
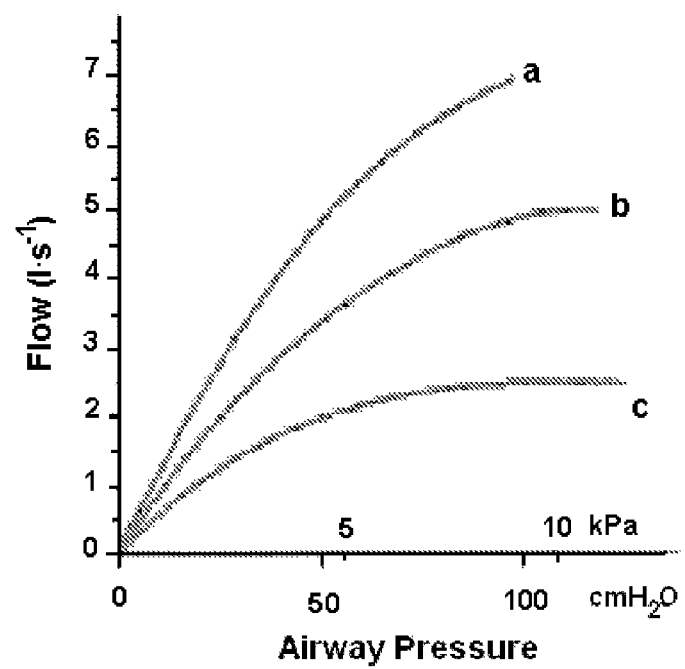
FIG. 7 shows the relation of airway pressure to flow for lung compartments of varying compliance.

As another alternative, lung compliance can be measured by analyzing the flow and pressure characteristics of the compartment during one or more cycles of respiration. In a normal, compliant compartment, the flow rate for a given pressure would be higher than it would be for a diseased lung. Since an elastic airway would be able to propel air through the airways better, the less elastic the airways of the compartment are, the lower the flow rate will be. An exemplary curve showing this is seen in FIG. 7. Curve "a" represents a normal lung with an associated healthy elasticity and compliance. Here, a high flow rate is achieved for a given pressure. Compartments that are affected by disease and have poor elastic recoil will tend to lower flow rates for a given pressure as observed in curves "b" and "c". By comparing a compartment with other compartments within the same lung, or by using population data, a user (or physician) may determine which compartment has less recoil (and thus is more diseased) than the others.

Figure 8:
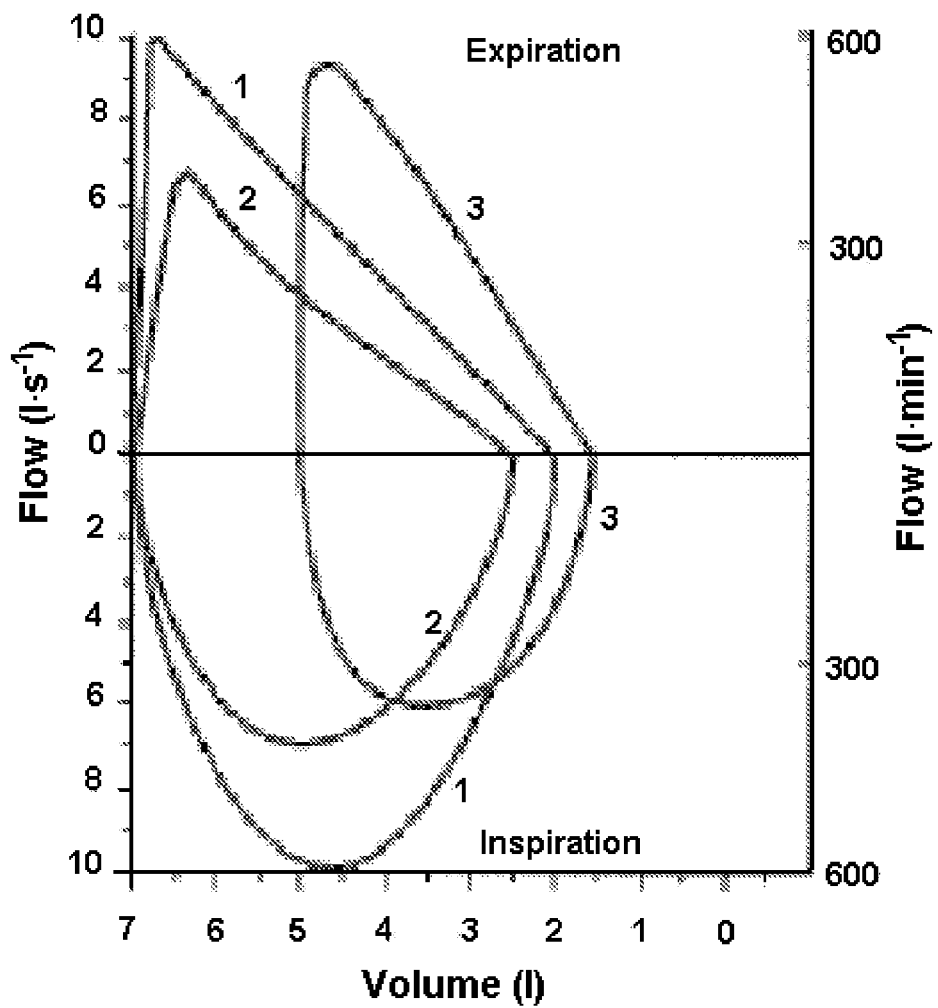
FIG. 8 shows a flow-volume loop for respiratory cycles corresponding to normal and diseased compartments.

Another method of determining the diseased state of the lung is to analyze the flow wave form and calculate the flow rate of the compartment with respect to a given volume). A healthy compartment would exhibit a higher peak flow rate for a given volume than its unhealthy counterparts. This is exemplarily seen in the graph in FIG. 8, which represents various resulting flow wave forms. Curve "1" represents normal expiration and shows that the peak flow is obtained just before the volume of air starts to increase. Flow thereafter decreases as volume increases. A similar and corresponding pattern is apparent in the inspiratory phase. Diseased compartments that have poor elastic recoil show lower peak flow for the same total volume, as shown in curves "2" and "3". Thus, by measuring a compartment's flow/volume characteristics, a less elastic and diseased compartment may be identified.

Figure 9:
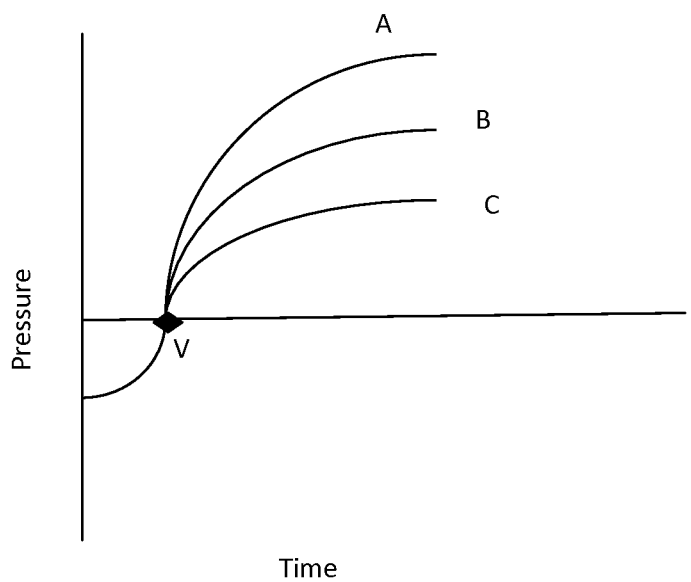
FIG. 9 illustrates the peak pressure obtained in both isolated and diseased targeted lung compartments.

Another method of determining the diseased state of the lung is to determine the peak pressure that would develop in a closed lung compartment. In order to do this, the catheter is placed in the lung and the balloon is inflated to isolate the TLC. At the end of on inhalation, the valve is closed, allowing the pressure to build up within the lung compartment until a peak pressure is reached. This is graphically represented in FIG. 9. At point "V", the valve is closed. Thereafter, a healthy lung compartment will exhibit a high peak pressure represented by curve "A". A diseased compartment will exhibit the peak pressure represented by curve "C". The compartment that is progressing towards a diseased state would be represented by curve "B".

Figure 10:
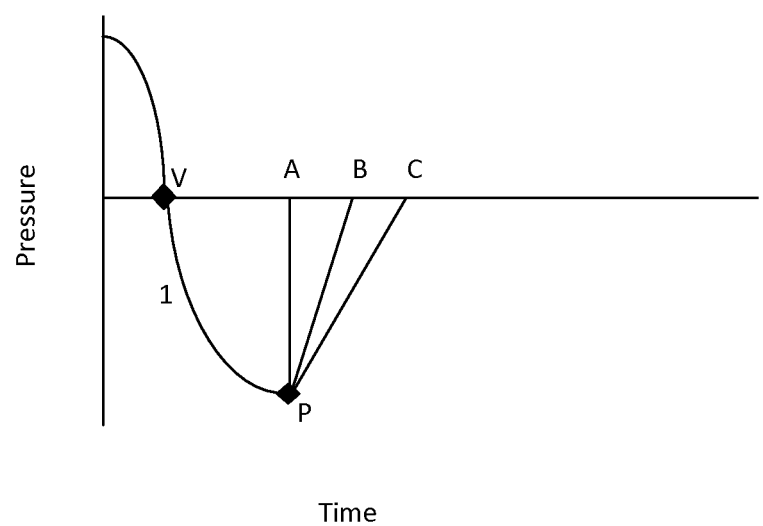
FIG. 10 shows a negative-pressure curve for both normal and diseased lung compartments.

Yet another diagnostic method is to determine the pressure that builds within the lung compartment when it is closed from all air exchange. Specifically, the negative pressure that builds within the lung compartment can be determined. In this method, the catheter is placed in the lung and the balloon is inflated and the patient is allowed to exhale. At the start of inhalation, the valve in communication with the catheter is closed, so that inhalation occurs in a closed system. This means that negative pressure would build within the targeted lung compartment, until it reaches a peak pressure. Thereafter, the valve is opened, and the rate of recovery of the pressure within the lung would be observed and analyzed. The longer the rate of recovery, the more diseased the lung. The graphical representation of this concept is illustrated in FIG. 10. At point "V", the valve is closed. Curve "1" represents the increase in the positive pressure of lung compartment that occurs as pressure builds up within the lung compartment. At the peak "P", which denotes the peak pressure, the valve is opened. A normal lung compartment (determined from other compartments within the same patient, or from within the general population), follows the pressure profile shown in curve "A". A diseased lung compartment will show a slow decrease in positive pressure and thus follow curve "C". A lung compartment that is in progression towards a diseased state will follow curve "B", which is a slower decrease than a healthy lung but a faster rate than an unhealthy lung.

Figure 11:
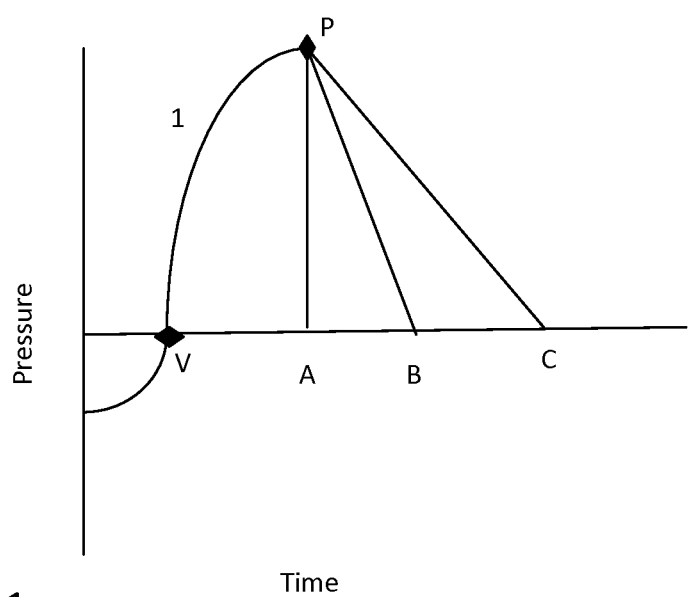
FIG. 11 shows a positive pressure curve for both normal and diseased lung compartments.

In a similar manner, the positive pressure build-up in a closed TLC can be used to determine the health of the lung compartment. As in the previous method, the catheter is placed in the lung and the balloon is inflated and the patient is allowed to inhale. At the start of exhalation, the valve associated with the catheter is closed, so that exhalation occurs in a closed system within the compartment. This means that positive pressure would build within the TLC. At the peak pressure, the valve would be opened and the rate of recovery of the pressure within the lung would be observed and analyzed. The longer the rate of recovery, the more diseased the lung. The graphical representation of this concept is illustrated in FIG. 11. At point "V", the valve is closed. Curve "1" represents the increase in the positive pressure of lung compartment that occurs as pressure builds up within the lung compartment. At the peak "P", which denotes the peak pressure, the valve is opened. A normal lung compartment (determined from other compartments within the same patient, or from within the general population), will follow the pressure profile of curve "A". A diseased lung compartment will show a slow decrease in positive pressure and thus follow curve "C". A lung compartment that is in progression towards a diseased state will show curve "B", which is a slower decrease than a healthy lung but a faster rate than an unhealthy lung.

Figure 12:
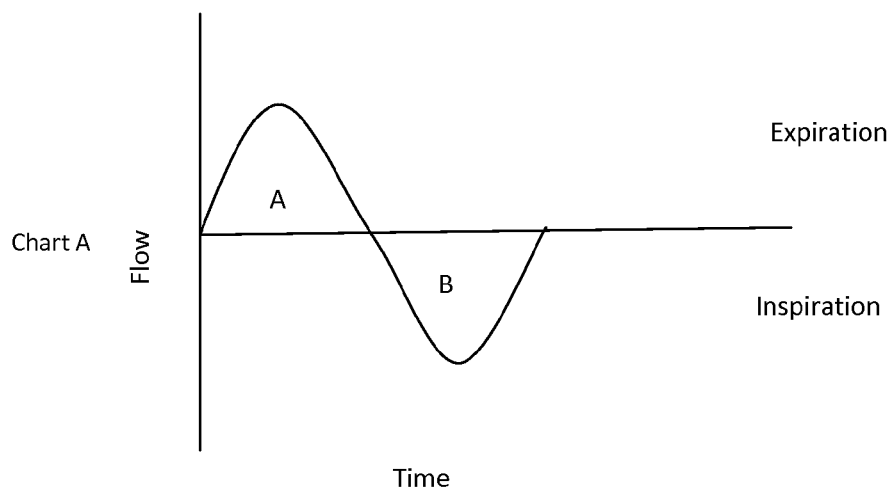
FIG. 12 illustrates detection of air trapping or a distal impediment to air flow.
Figure 12:
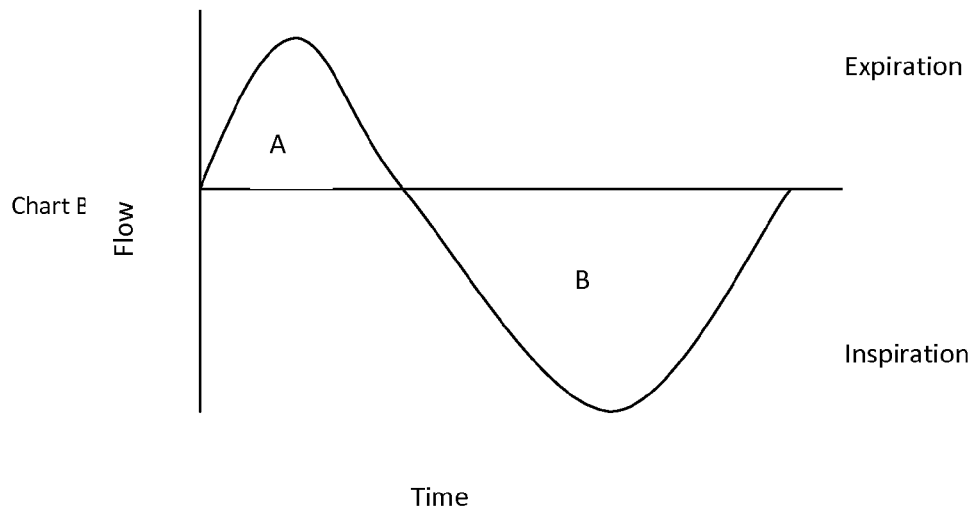

Another use for the catheter, in addition to determining the compliance of the airways, is to detect whether air is being trapped distal to the measurement site, as well as determining whether an impediment (e.g., an occlusion, a blocked airway, etc.), exists distal to the measurement site. In doing so, the volume of air being received into the catheter is measured over time, as seen in FIG. 12. Specifically, as shown in chart "a", in a normal lung, the volume of air being inspired ("A") is roughly equivalent to the volume of air being expired ("B"). However, as shown in chart "b", in a diseased lung with significant air trapping, the volume of air being inspired ("A") would be less than the volume of air being expired ("B"). The similar principle can be used to detect an impediment in the form of a collapsed airway or an occlusion distal to the catheter. Similarly, pressure can be analyzed over time, with higher pressures during expiration indicating air trapping and the presence of an occlusion. The results expected would be similar to the graphs shown in FIG. 12.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for determining a disease state of-a portion of a lung in a patient, the method comprising:
   introducing a catheter into an airway leading to a targeted lung compartment, the catheter comprising a distal end, a proximal end, and a lumen therebetween, wherein the distal end comprises an expandable occluding element which is configured to sealingly engage the airway, wherein the proximal end comprises an inflation port to expand the occluding element, and wherein the lumen is in-line with at least one sensor for measuring pressure in the targeted lung compartment, and wherein a solenoid valve is in-line or within the lumen;
   expanding an occluding member disposed on or near a distal end of the catheter to form a seal with an inner wall of the airway to thus isolate the targeted lung compartment;
   closing the solenoid valve thereby preventing airflow to or from the targeted lung compartment;
   measuring pressure in the targeted lung compartment while the solenoid valve is closed using a pressure sensor coupled with the lumen of the catheter;
   allowing the pressure to build within the targeted lung compartment while the solenoid valve is closed until a peak pressure is reached;
   determining the peak pressure in the targeted lung compartment while the solenoid valve is closed;
   opening the solenoid valve after the peak pressure is reached;
   determining a rate of recovery of the pressure in the targeted lung compartment from the peak pressure while the solenoid valve is open; and
   determining a disease state of the targeted lung compartment based on the rate of recovery of the pressure in the targeted lung compartment from the peak pressure; wherein determining the disease state comprises comparing the rate of recovery of the pressure in the targeted lung compartment from the peak pressure to a rate of recovery in another lung compartment within the same patient, or a rate of recovery within a general population.

2. The method of claim 1, wherein the valve is closed at the end of inhalation thereby allowing the pressure to build up in the targeted lung compartment.

3. The method of claim 1, wherein the valve is closed at the start of inhalation thereby allowing negative pressure to build up in the targeted lung compartment.

4. The method of claim 1, wherein the valve is closed at the start of exhalation thereby allowing positive pressure to build up in the targeted lung compartment.

* * * * *